(12) United States Patent
Marton et al.

(10) Patent No.: US 7,303,916 B2
(45) Date of Patent: Dec. 4, 2007

(54) SUSTAINED TOTIPOTENT CULTURE OF SELECTED MONOCOT GENERA

(75) Inventors: Laszlo Marton, Chapin, SC (US); Mihaly Czako, Columbia, SC (US)

(73) Assignee: University of South Carolina, Columbia, SC (US)

( * ) Notice: Subject to any disclaimer, the term of this patent is extended or adjusted under 35 U.S.C. 154(b) by 114 days.

(21) Appl. No.: 10/982,254

(22) Filed: Nov. 5, 2004

(65) Prior Publication Data

US 2005/0102719 A1    May 12, 2005

Related U.S. Application Data

(63) Continuation of application No. 10/068,584, filed on Feb. 5, 2002, now Pat. No. 6,821,782.

(60) Provisional application No. 60/266,067, filed on Feb. 5, 2001.

(51) Int. Cl.
*C12N 5/02*    (2006.01)

(52) U.S. Cl. ............... 435/430.1; 435/430; 435/420

(58) Field of Classification Search ............... 435/420, 435/430.1, 430
See application file for complete search history.

(56) References Cited

U.S. PATENT DOCUMENTS

| | | | |
|---|---|---|---|
| 4,337,683 A | 7/1982 | Backus | 84/383 |
| 5,829,192 A | 11/1998 | Gatliff | 47/58 |
| 5,876,484 A | 3/1999 | Raskin et al. | 75/711 |
| 5,917,117 A | 6/1999 | Ensley et al. | 75/711 |
| 5,917,177 A | 6/1999 | Ensley et al. | 75/711 |
| 5,927,005 A | 7/1999 | Gardea-Torresdey et al. | 47/58.1 |
| 5,965,796 A | 10/1999 | Meagher et al. | 800/298 |
| 6,087,547 A | 7/2000 | Marton et al. | 588/206 |
| 6,153,812 A * | 11/2000 | Fry et al. | 800/288 |
| 6,190,526 B1 | 2/2001 | Ho | 204/515 |
| 6,284,945 B1 | 9/2001 | Dudits et al. | 800/265 |
| 6,821,782 B2 | 11/2004 | Marton et al. | 435/430 |
| 7,052,912 B1 * | 5/2006 | Woods et al. | 435/430.1 |
| 2002/0166149 A1 | 11/2002 | Marton et al. | |
| 2002/0174455 A1 | 11/2002 | Marton et al. | |

FOREIGN PATENT DOCUMENTS

HU    216536 B    2/1990

(Continued)

OTHER PUBLICATIONS

Mendoza, Armeina and Yutzo Futsuhara. "Histological Observations of Plant Regeneration in Rice (Oryza sativa L.) Calli" Japan J. Breed. 42:33-41 (1992).*

(Continued)

*Primary Examiner*—Wendy Haas
(74) *Attorney, Agent, or Firm*—Nelson Mullins Riley & Scarborough, LLP

(57) ABSTRACT

A method is provided for generating sustained totipotent tissue cultures of a plant of the Class Monocotyledonae, and for micropropagating such plant in vitro, wherein immature inflorescence are cultivated to produce totipotent tissue which is suitable for sustained maintenance and propagation. Greening of the tissue can be induced under light and the multishoot culture can multiply by microtillering. Foreign genes can be introduced into the tissue if desired, and the transgenic plants can be used in phytoremediation technologies in the field and in phytoreactors independently of seasons.

24 Claims, 4 Drawing Sheets

FOREIGN PATENT DOCUMENTS

| HU | 220186 B | 3/1990 |
|---|---|---|
| HU | P9007120 | 11/1990 |
| WO | WO 00/66757 | 11/2000 |
| WO | WO 02/063024 A3 | 8/2002 |

OTHER PUBLICATIONS

Christou, Myrsini, et al., "Giant Reed (*Arundo donax L.*) Network Improvement, Productivity and Biomass Quality," AFB-net NEWS-LETTER- Sep. 2, 1998, Austria, pp. 4-5, downloaded from website address www.etsu.com/Europ/AFB/contents.htm.

Molnar, S.J., et al., "Initiation of totipotent tissue cultures from undeveloped axillary and secondary ears," downloaded from website www.agron.missouri.edu/mnl/54/41molnar.html on Feb. 4, 2002.

Perdue, Robert E., Jr., "*Arundo donax*: Source of Musical Reeds and Industrial Cellulose," originally published in Economic Botony, 1958, U.S.A., downloaded from website www.wuarchive.wustl.edu/doc/misc/org/doublereeds/general/cane.html on Feb. 4, 2002.

Taylor, Marsha, "Cultivation of California *Arundo Donax*," 1971, revised and annotated 1996, U.S.A., downloaded from website www.oboe.org/donax.htm on Feb. 4, 2002.

Veselack, Marilyn S., "*Arundo donax*: The Source of Natural Woodwind Reed," U.S.A., downloaded from website www.idrs.colorado.edu/Publications/DR/DR2.1/arundo.html on Feb. 4, 2002.

"Biology of *Arundo donax* (Giant reed, giant cane)," downloaded from website www.smslrwma.org/ADBiology.htm on Feb. 4, 2002.

"Invasive Alien Plant Species of Virginia," written with assistance from Stephen E. Zurek, Virginia Polytechnic Institute and State University, downloaded from website www.vnps.org/invasive/FSARUN.html on Feb. 4, 2002.

"Plants Profile," downloaded from website www.plants.usda.gov/cgi_bin/plant_profile on Feb. 4, 2002.

"Propagation of *Arundo donax*—Giant Reed," downloaded from website www.grasses.co.uk/arundo/arundo_m.htm on Feb. 4, 2002.

"Totipotent Regeneration," Access Excellence, About Biotech, © 1999 @ the National Health Museum, downloaded from website www.accessexcellence.org/AB/WYW/fink/fink_7.html on Feb. 4, 2002.

Partial international search dated Jan. 14, 2003. Annex to the Invitation to Pay Additional Fees (PCT/US 02/03494).

Article published in Aquatic Botany 2000, vol. 68, pp. 239-247 by S.M.D. Rogers and K.S. Sarma entitled Plant Regeneration from Seedling Explants of *Juncus Effusus*.

Article published in Plant Cell Reports 1998, vol. 17, pp. 251-255 by C. Chang and W.C. Chang entitled Plant Regeneration from Callus Culture of *Cymbidium Ensifolium*var. Misericors.

Article published in Biotechnology Letters Apr. 1994, vol. 16, No. 4, pp. 397-400 by A. Ali and W. Sawahel entitled Callus Induction and Maintenance of *Zea Mays*Kernels.

PCT Written Opinion (PCT Rule 66) mailed Dec. 15, 2004, International Application No. PCT/US02/03494.

LI, X. et al. Tissue Culture and Regeneration in the Halophytic Grass Spartina alterniflora Loisel. World Congress on Cell and Tissue Culture. Jun. 23-24 1992, see all.

LI, X. et al. Tissue Culture and Plant Regeneration of Big Cordgrass, Spartina Cynosuroides: Implications for Wetland Restoration. Wetlands. Dec. 1996, vol. 16, No. 4, pp. 410-415, see all.

LI, X. et al. Plant regeneration from callus cultures of salt marsh hay, Spartina patens, and its cellular-based salt tolerance. Aquatic Botany. 1995, vol. 51, No. 1-2, pp. 103-133, see Abstract.

Gallagher J.L. et al. Selecting Halophytes for Agronomic Value: Lessons from Whole Plants and Tissue Culture. Strategies for Utilizing Salt-affected Lands. 1993, pp. 414-425, see all.

Anonymous. http://www.wapms.org/plants/spartina.html.

PCT International Examination Report (PCT Rule 36 and Rule 70) mailed Jun. 8, 2005, Completion Date Jun. 2, 2005, International Application No. PCT/US02/03494.

Article published in Plant Cell, Tissue and Organ Culture 2000, vol. 62, pp. 21-25 by Y. Lin et al. entitled Plant Regeneration from Callus Culture of a Paphiopedilum Hybrid.

Partial international search dated Jan. 8, 2003. Annex to the Invitation to Pay Additional Fees (PCT/US 02/03493).

Abstract of article published in American Journal of Botany Jun. 1998, vol. 85, No. 6, p. 89, XP009002295 by C. Linder et al entitled Tissue Culture and Regeneration of the Giant Reed.

Article from Sustainable Agriculture for Food, Energy and Industry, 1998, James & James (Science Publishers) Ltd., pp. 249-253 by Szilard Toth and Gunda Mix-Wagner entitled Embryogenic callus induction of different explants of *Miscanthus sinensis, Miscanthus x giganteus and Arundo donax*genotypes.

Element Stewardship Abstract for *Arundo donax*for The Nature Conservancy by Marc Hoshovsky.

Monthly Archive, Oct. 1999, entitled Re: TC protocols for *Arundo donax* at http://plant-tc.coafes.umn.edu/listserv/1999/log9910/msg00105.html.

Abstract from Agronomy Abstracts, 2000, p. 181 by Somleva, M.N. and B.V. Conger entitled Angrobacterium mediated transformation of orchardgrass and switchgrass.

PCT Written Opinion mailed Nov. 22, 2004, International Application No. PCT/US02/03493.

Article from Plant Culture Concepts and Laboratory Exercises, 1996, pp. 12-25 by E. G. Sutter entitled General laboratory requirements, media and sterilization methods.

Article from Plant Culture Concepts and Laboratory Exercises, 1990, pp. 459-525 by Hudson T. Hartmann, et al. entitled Plant Propagation Principles and Practices.

\* cited by examiner

SUSTAINED TOTIPOTENT CULTURE OF SELECTED MONOCOT GENERA

CROSS REFERENCE TO RELATED PATENTS AND PATENT APPLICATIONS

The present application is a continuation of U.S. patent application Ser. No. 10/068,584, filed Feb. 5, 2002 now U.S. Pat. No. 6,821,782, which claimed priority from U.S. Provisional Patent Application Ser. No. 60/266,067, filed Feb. 5, 2001, each of which is incorporated herein by reference in its entirety.

BACKGROUND OF THE INVENTION (1) Field of the Invention

The present invention relates to a method for the production of plants of the Class Monocotyledonae ("monocots") on a large scale, and more particularly to a method for the production of cloned monocot plants with the potential for the production of transgenic monocot plants, and to the monocot plants produced by the method.

(2) Description of the Related Art

Induction of regenerable tissue cultures from monocot species is conventionally attempted from immature embryos or immature inflorescences. Both approaches have been shown to work on *Typha glauca, T. angustifolia* and *T. latifolia* (Rogers, S. D. et al., *Plant Cell Reports*, 18:71-75 (1998). No report of tissue culturing of the fourth North American species, *T. dominguensis*, has been found.

Tissue culture of only two *Juncus* species has been reported, (Sarma, K. S. et al., *Plant Cell Rep.*, 17:656-660 (1998), Sarma, K. S. et al., *Aquatic Botany* 68: 239-247 (2000), and no reports of regenerable tissue cultures have been found for species of the grass, *Erianthos giganteus*, sedges of the genera *Cyperus* and *Carex*, and bulrushes of the genus *Scirpus*.

Plant regeneration from cultured cells of the great majority of monocot (mostly graminaceous) species that have been reported so far, is achieved from callus initiated on high concentrations of a strong auxin, such as 2,4-dichlorophenoxyacetic acid (2,4-D) (Conger, B. V. et al., pp. 59-68 in *Current Issues in Plant Molecular and Cellular Biology*, (1995)).

One monocot, *Arundo donax* L., or Giant Reed, of the Order Poales and the Family Poaceae (Gramineae), is one of the largest grasses in the world, and is an attractive, robust, perennial reed. Tucker, G. C., *J. Arnold Arb.*, 71:145-177 (1990). The very strong, somewhat woody, clustering culms, which grow from horizontal knotty rootstocks, are known to grow to a height of 8-10 meters and to have a diameter of from 1 to 4 cm. Bailey, L. H., Manual of cultivated plants: Most commonly grown in the continental United States and Canada, Rev. Ed., MacMillan, New York, (1954); and Mabberley, D. J., The plant-book: a portable dictionary of the vascular plants, $2^{nd}$ Rev., Cambridge Univ. Press, Oxford (1997). It is one of the largest of the herbaveous grasses and has fleshly, creeping rootstocks that form compact masses from which arise tough fibrous roots that penetrate deeply into the soil. The culms commonly branch during the second year of growth and are hollow with walls of 2 to 7 mm thick.

The plant is known by a variety of common names, including carrizo, bamboo reed, Danubian reed, donax cane, Italian reed, Provence cane and Spanish reed. *A. donax* probably originated from the freshwaters of the warm regions of eastern Asia. It has been in cultivation in Asia, North Africa, and the Middle East for thousands of years and also in North and South America, Australia and South Africa, during the past century. Further information on the culture of *A. donax* can be found, for example, in Bell, G. P. *Ecology and management of Arundo donax*, and *approaches to riparian habitat restoration in Southern California*, in *Plant Invasions: Studies From North America and Europe*, Brock, J. H. et al., Eds. pp.103-113, Backhuys Publishers, Leiden (1997); Perdue, R. E., Econ. Bot., 12:368-404 (1958); Rossa, B. et al., *Bot. Acta*, 111:216-221 (1998); Roys, R., *Ethnobotany of the Maya: The Department of Middle American Research*, M.A.R. Series Pub. 2, Tulane U., New Orleans (1931); Zahran, M. A. et al., *The vegetation of Egypt*, Chapman & Hall, London (1992); and Zohary, M., *Plant Life of Palestine*, Ronald Press, New York (1962).

Plants from the Class Monocotyledonae, such as *A. donax*, are often multipurpose plants. Giant reed, for example, has been used for 5,000 years for pipe instruments and is the source for reeds for clarinets and organ pipes. Even with today's modern technology, most of the reeds for woodwind musical instruments are still made from *A. donax* culms.

Giant reed is also used for erosion control and has great potential for use as an energy crop. Szabo, P., et al., *J. Anal. Appl. Pyrolysis*, 36:179-190 (1996). The culms are also used for fishing rods, walking sticks, mats and lattices in the construction of adobe huts. Giant reed is also a source of industrial cellulose for paper and rayon making, and for the production of other polysaccharides. Neto, C. P. et al., *Ind. Crops & Prods.*, 6:51-58 (1997). It has even been considered as a source of pulp for the making of paper. Perdue, R., *Arundo donax: Source of Musical Reeds and Industrial Cellulose*, www.wuarchive.wustl.edu/doc/misc/org/doublereeds/general/cane.html.

Giant reed grows very rapidly. When conditions are favorable, growth at a rate of 0.3 to 0.7 meter per week for several weeks is not unusual. Young culms typically grow to their full diameter within the initial growing season, but their walls increase in thickness thereafter.

Outside its native range and the Mediterranean, however, the plant is sterile; it flowers, but does not produce viable seed. It reproduces vegetatively efficiently from fragments of stems and rhizomes. Boose, A. B. etal., *Weed Res.*, 39:117-127 (1999). Traditional horticultural propagation of giant reed is by division of rhizomes. However, the propagation of giant reed by either rhizome division, or by traditional seed culture require a significant amount of time and effort between the initiation of division, or planting, and the successful establishment of a growing plant. Moreover, conventional methods of propagation provide limited opportunity for genetic manipulation, and, in the case of seeds, do not permit genetic control of the resulting progeny. Such conventional techniques also require large areas for the production of a sufficient number of plants to be useful in programs for the production of fuel or biomass, or for use in bioremediation programs.

Giant reed is only one of the monocots that exhibits such multiple uses. Whether used as ornamentals, sources of energy, or as useful vehicles to carry out industrial processes, such grass-like plants are important.

Accordingly, it would be useful to be able to provide a method by which plants of the Class Monocotyledonae, and in particular, plants such as those of *Juncus* spp., *Scirpus* spp., *Cyperus* spp., *Carex* spp., *Erianthus* spp., and *Typha* spp, could be propagated even in areas in which plants of these genera are sterile and in a manner that would require shorter time, less effort and less area than conventional methods. In particular, it would be useful if a method could be provided that permitted better genetic manipulation and control of the plants. Moreover, it would also be useful if the method was independent of seasons and was sustainable at a high rate of propagation.

SUMMARY OF THE INVENTION

Briefly, therefore the present invention is directed to a novel method for the production of totipotent tissue culture of a plant of the Class Monocotyledonae, the method comprising: selecting an explant of living tissue from the plant; and cultivating the tissue on a primary medium to produce totipotent tissue culture.

The present invention is also directed to a novel method for the micropropagation of a plant of the Class Monocotyledonae, the method comprising: selecting an explant of living tissue from the plant.; cultivating the tissue on a primary medium to produce a totipotent tissue culture; cultivating the totipotent tissue on a secondary medium to produce complete plantlets having roots and shoots; and acclimating the plantlets in soil.

The present invention is also directed to a novel plant of the Class Monocotyledonae that is produced by the method described first above.

The present invention is also directed to a novel transgenic plant of the Class Monocotyledonae that is produced by the method described first above, but, in addition, transferring a heterologous gene into the totipotent tissue.

The present invention is also directed to a novel method for removal of an environmental pollutant from wastewater, the method comprising: providing at least 10 plants that possess the same genetic characteristics; establishing the plants in a liquid medium; and contacting the roots of the plants in the liquid medium with an environmental pollutant, thereby causing the environmental pollutant to be removed from the liquid medium.

The invention is further directed to a method for bioremediation of an environmental pollutant from a land area that comprises providing at least 10 plants from the Class Monocotyledonae that possess the same genetic characteristics, establishing the plants in soil, and contacting the roots of the plants with the environmental pollutant in the land area, thereby causing the environmental pollutant to be removed from the land area.

Among the several advantages found to be achieved by the present invention, therefore, may be noted the provision of a method by which plants of the Class Monocotyledonae, and in particular such as those of *Juncus* spp., *Scirpus* spp., *Cyperus* spp., *Carex* spp., *Erianthus* spp., and *Typha* spp. can be propagated even in areas in which plants of these genera are sterile. Such method also provides for propagation that can be carried out in a manner that would require shorter time, less effort and less area than conventional methods. Such method also provides for better genetic manipulation and control of the plants. The novel method also provides for the ability to carry out these activities in a manner that is independent of seasons and is sustainable at a high rate of propagation.

DETAILED DESCRIPTION OF THE PREFERRED EMBODIMENTS

Figure 1:
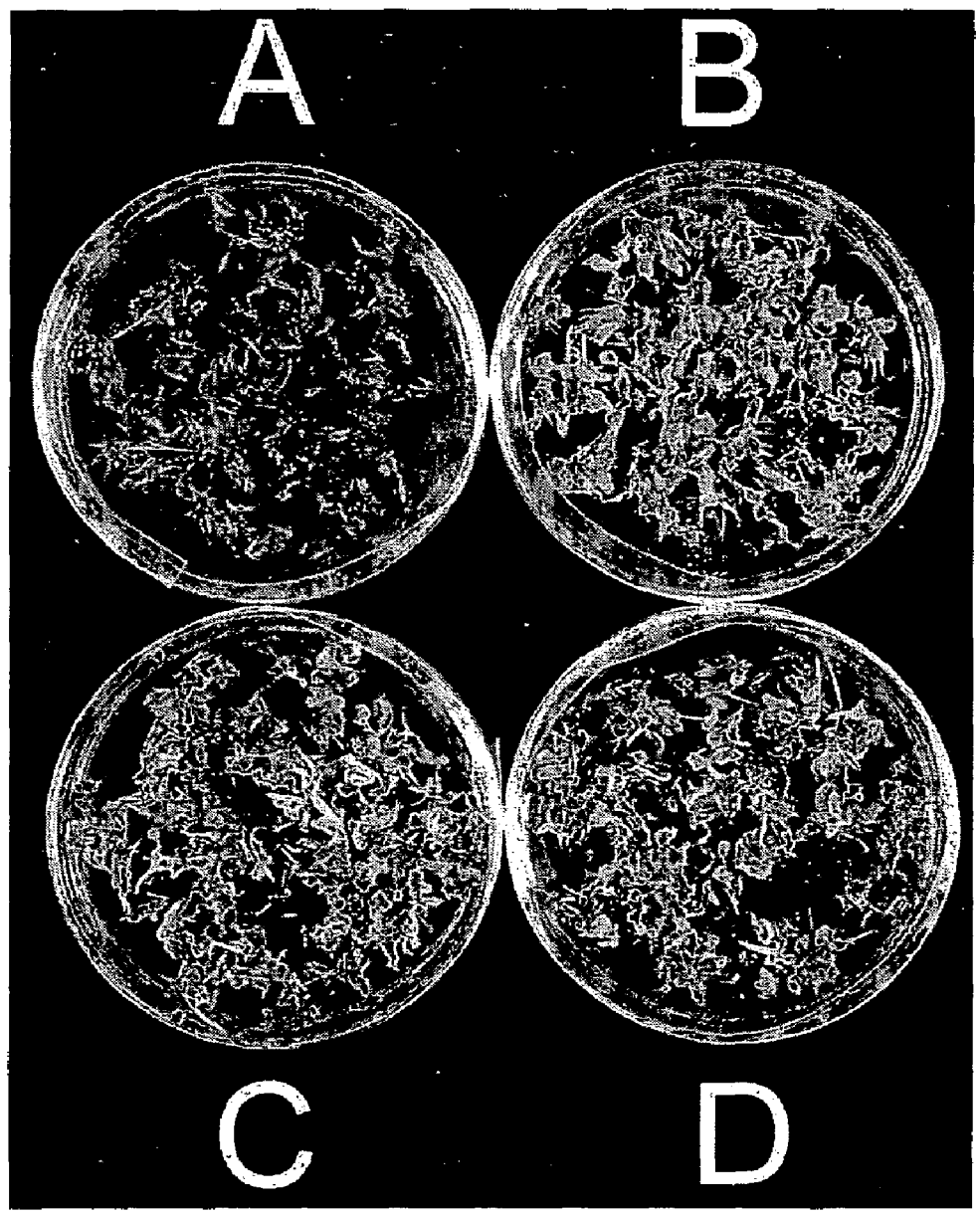
FIG. 1 shows the development of herbicide resistant embryogenic tissue on explants cocultivated with *Agrobacterium tumefaciens* (FIG. 1C), which can be contrasted with control explants (which were not contacted with *A. tumefaciens*) that were killed by 10 mg/l of phosphinothricin (FIG. 1A), and control explants that have developed callus in the absence of phosphinothricin (FIG. 1B), and cocultivated explants that have developed callus in the absence of phosphinothricin (FIG. 1D)

In accordance with the present invention, it has been discovered that regenerable tissue can be produced from tissues of plants of the Class Monocotyledonae, and in particular, plants of *Juncus* spp., *Scirpus* spp., *Cyperus* spp., *Carex* spp., *Erianthus* spp., *Typha* spp, *Cynodon dactylon*, *Digitaria sanguinalis*, *Erianthus giganteus*, *E. strictus*, *Miscanthus sinensis*, *Paspalum urvillei*, *Panicum dichotomum*, *Poa* sp 1, *Poa* sp 2, *Setaria gigantea*, *Sorghum halepense*, *Spartina alterniflora*, *S. cynosuroides*, *S. pectinata*, *S. spartinae*, and *S. patens* of Poaceaea (grasses family); *Carex acuta*, *Carex* sp 2, *Cyperus esculentus*, *Cy. giganteus*, *Cy. haspan*, *Cy. iria*, *Cy. odoratus*, *Cy. pseudovegetus*, *Cy. retrorsa*, *Scirpus acutus*, *S. americanus*, *S. californicus*, and *S. validus* of Cyperaceae (sedges family); *Juncus articulatus*, *J. compressus*, *J. dichotomus*, *J. effusus*, *J. roemerianus*, and *J. tenuis* of Juncaceae (rushes family); as well as *Typha angustifolia*, *T. dominguensis*, and *T. latifolia* of Typhaceae (cattails family) by a method wherein the tips of field-grown or greenhouse grown pre-flowering shoots with leaf sheaths completely enclosing a developing but yet unemerged immature inflorescence, whose surface has been sterilized, are stripped of the leaves and the inflorescences are cut into cross-sectional pieces, which are then cultivated on a solid-type primary medium containing plant hormones. Multi-shoot formation, but not elongation, occurs on the primary medium, and so the method is therefore suitable for sustained maintenance and propagation of the totipotent tissue culture.

As used herein, the term "totipotent" means having unlimited capability to produce any type of cell. Totipotent cells have the capability to turn (or "specialize") into all of the tissues and organs that are present in the completely developed plant. In other words, totipotent cells have the capability to regenerate into whole plants.

Another aspect of the present invention is a method for regeneration of complete plantlets with roots and partially elongated shoots which continue to multiply by microtillering on a solid-type secondary medium containing a plant hormone.

A further aspect of the invention is a method for inducing shoot elongation on a solid-type tertiary medium containing no plant hormones.

The totipotent tissue culture is suitable for introduction of foreign genes by means of cocultivation of the totipotent tissues or the plantlets derived therefrom with *Agrobacterium tumefaciens*, or by the biolistic and other direct DNA transfer methods of injecting heterologous genetic material into the totipotent regenerable tissue culture. Suitable techniques for carrying out the insertion of heterologous genes into plants or plant tissues are described, for example, in Barcelo, P. et al., *Advances in Botanical Research Incorporating Advances in Plant Pathology*, 34:59-126 (2001); Christou, P., Particle bombardment methods in cell biology, 50:375-382 (1995); Christou, P., *Field Crops Res.*, 45(1-3): 143-151 (1996); and Christou, P., *Trends in Plant Sci.*, 1(12):423-431 (1996).

In general, the present method includes the following steps: An explant of living tissue of the monocot plant of interest is obtained. The explant is cultivated in medium and under conditions so that totipotent tissue is generated. The cultivation can be carried out in the dark. In a preferred embodiment, greening is induced in the totipotent tissue generated in the cultivation step by subjecting the tissue to light. The totipotent tissue that is generated in the cultivation step can be maintained on the same medium and under the same conditions in order to continue the generation of totipotent tissue, or it can be allowed to form roots and shoots. Regenerating tissue having roots and shoots can then be cultivated further on hormone-free medium in order to develop plantlets having elongated leaves and healthy root systems. The plantlets can then be transferred to soil for acclimation. When the plantlets have become acclimated in soil, they can be transplanted to any desired location, including the location for final planting.

When an explant of living tissue from a monocot plant is obtained for use in the present method, the tissue can be living tissue that is obtained from any source. The genetic material can be obtained from a living monocot plant, or it can be obtained as tissue culture, or any other tissue, from any one of the steps of the present method.

When the explant is obtained from a living monocot plant, it is preferred that is obtained from an immature inflorescence. An example of a starting material for the explant of the present invention can be obtained from the tips of field-grown or greenhouse-grown pre-flowering shoots with leaf sheaths completely enclosing the developing, but yet unemerged immature inflorescence. It has been found that an immature inflorescence enclosed in leaf sheaths before blooming is preferred since it exhibits a higher yield of regenerable tissue than other tissue sources.

To prepare the explant for cultivation, all but the terminal leaf sheaths are carefully stripped so as not to expose the inflorescence. The shoot tips can then be sanitized, or surface sterilized. One method of surface sterilization is by immersing the shoot tips in a solution of 5× diluted commercial bleach containing 10% v/v ethanol and 0.1% Tween 80 surfactant for 15 minutes. The shoot tips can then be rinsed three times with sterile water prior to further use. Such sterilization reduces or eliminates environmental bacterial contamination.

The inflorescence is then excised from all leaf sheaths under aseptic conditions and is cut or chopped into cross-sectional pieces. Any sterilized sharp blade, knife, or scalpel can be used for this step. By cutting an aseptic immature inflorescence containing a number of meristematic regions into cross-sectional pieces, the formation of regenerable tissue is induced.

The pieces of the cut-up inflorescence are then cultivated in a primary cultivation step in which totipotent tissue is generated. It is preferred that the primary cultivation be carried out in the dark and at approximately room temperature. It is also preferred that the cultivation be carried out on a solid-type medium that contains plant hormones. The duration of the primary cultivation step is sufficiently long for multishoot tissue formation, but not elongation, to occur. It is preferred that the primary cultivation step have a duration of from about two weeks to about eight weeks, and even more preferred that it has a duration of about four weeks, yet more preferred, that the primary cultivation step have a duration of four weeks.

A preferred temperature range for the primary cultivation step is from about 15° C. to about 35° C., a temperature range of about 20° C. to about 30° C. is more preferred, a temperature of about 26° C. to 28° C. is even more preferred, and a temperature of about 25° C. is yet more preferred.

The medium that is useful for the primary cultivation step can be a basal medium for plant tissue culture. Examples of suitable medium include, without limitation, DM-8 medium (as described below), or MS medium, or Gamborg's B5 medium at full or ½ strength. It is preferred that the primary medium is supplemented with a plant hormone. Examples of suitable plant hormones include auxins, such as 2,4-dichlorophenoxyacetic acid, and picloram. In preferred embodiments, these hormones can be employed in combination with cytokinins, such as benzyladenine, zeatin, or thidiazuron.

One example of a medium for the primary cultivation step can be prepared by adding to sterile water MS (Murashige and Skoog, 1975) basal salts (Sigma Fine Chemicals, St. Louis, Mo.), 4.3 g/l; Miller's salt solution (6% w/v, $KH_2PO_4$), 3 ml; myo-inositol, 100 mg/l; Vitamix (Marton and Browse, *Plant Cell Reports*, 10: 235-239 (1991), 2 ml.; sucrose, 30 g/l; supplemented with the plant growth regulators adenine hemisulfate, 400 μM; picloram, 0.12 mg/l; indole-3-butyric acid, 1 mg/l; 2,4-dichlorophenoxyacetic acid, 0.5 mg/l; isopentenyladenine, 0.5 mg/l; trans-zeatin, 0.5 mg/l; and thidiazuron, 3 mg/l, and solidified with Phytagel (Sigma Fine Chemicals) 2 g/l.

It is preferred that a gellant, such as Gellan gum, for example, Phytagel, available from Sigma Co., St. Louis, Mo., is also employed in the medium at conventional rates. Less purified Gellan substitutes, such as Gelcarin, agarose, or agar can also be used.

It is preferred that the pH of the medium for the primary cultivation step is adjusted to 5.8 before the medium is sterilized. By way of example, the medium can be sterilized in a pressure cooker for 25 minutes at a temperature of about 109° C. and at a pressure of about 35 kPa.

The warm medium may be poured into a sterile petri dish and allowed to cool to room temperature. The chopped explant material can then be distributed upon the surface of the gelled medium, and the petri dish covered with a lid to preserve sterility. The covered dish can then be placed in a location suitable for maintaining the temperature as discussed above.

It is also preferred that the tissue being cultured is kept in the dark during the primary cultivation step. However, as an alternative, the genetic material may be subjected to continuous illumination during the primary cultivation step. If continuous illumination is employed, it is preferred that it be of an intensity of about 30-50 μmol $m^{-2}s^{-1}$, and be a mixture of incandescent and cool white fluorescent tubes.

During the primary cultivation step, multishoot formation occurs from the cut-up explant tissue, but without significant shoot elongation. The culture at this point comprises totipotent tissue (which may also referred to herein as totipotent, or regenerable, tissue culture). Small clusters of totipotent tissue can then be transferred to fresh medium for the production of more shoots, or they may be transferred to hormone-free medium for the development of root systems and elongated leaves. Therefore, the totipotent tissue can be used as a regenerable source of genetic material for sustained maintenance and propagation.

In a preferred embodiment, greening of the etiolated dark-grown tissue produced in the primary cultivation step may be initiated under light in about two or three days in the culturing room with artificial illumination.

After completion of the primary cultivation step, the totipotent tissue can then be cultivated in a secondary cultivation step in which shoot multiplication continues and complete plantlets are induced. The medium that is useful for the secondary cultivation step can be DM-5 medium (which is described below), or it can be a basal medium for plant tissue culture such as MS, or Gamborg's B5 medium at full or ½ strength. It is preferred that the medium is supplemented with a plant hormone, and it is more preferred that the plant hormone is present at a concentration that is lower than is used in the primary medium. Examples of plant hormone that can be employed include cytokinins, such as benzyladenine, zeatin, and thidiazuron. Thidiazuron is a preferred hormone.

In one example, the medium for the secondary cultivation is prepared by adding to sterile water from about 0.01 to about 1 mg/l, preferably about 0.02 ml/l, of a cytokinin, such as thidiazurone, 30 g/l of sucrose, and about 3 ml of Miller's salt solution (6% w/v $KH_2PO_4$). The medium can be gelled and sterilized as described for the primary medium.

Totipotent tissue from the primary cultivation step can then be used to inoculate the secondary medium. The inoculated secondary cultivation medium is then cultured, either in the dark or under continuous light, at about room temperature, for a period of from about one week to about four weeks. At the end of the secondary cultivation, the culture will contain complete plantlets with roots and partially elongated shoots.

At this point, the plantlets can be either moved directly to soil for acclimation, or they can be cultivated in a tertiary cultivation step to permit shoot elongation prior to transfer to soil.

It is preferred that the plantlets are moved into a tertiary medium that is similar to the medium that is used for the secondary cultivation step, but which is free of plant hormones. The tertiary cultivation step is carried out at substantially room temperature, and for a duration of about four weeks.

The plantlets are then transferred from the tertiary medium to soil for acclimation.

When the plantlets have become acclimated in soil, they can be transplanted to any desired location, including the location for final planting.

Monocot plants include species that have a number of diverse uses, some of which are commercially important. Giant reed (A. donax L.), for example has a phenomenal growth rate of up to 6.3 cm per day, and fast regeneration after cropping. A. donax attains heights more than 4 meters in less than one growing season. This growth rate is supported by an unusually high photosynthetic capacity (maximum photosynthetic $CO_2$ uptake between 19.8 and 36.7, mol $m^{-2}s^{-1}$), and a very large water use (2,000 l/m² of standing A. donax). A. donax can produce up to 100 tons per hectare of above-ground biomass. In North America and other locations, it forms pure stands because of the lack of natural predators and competitors. It does not provide habitat or food for wildlife because it contains chemicals that protect if from insects and grazers. It can grow in water, and can oxidize sulfides and reduce heavy metal ions by releasing oxygen into the anaerobic organic sediment. The fibrous roots of the creeping rootstock penetrate up to 4.9 m deep in sand. A. donax thrives in both alkaline and acidic conditions in mild drainage and absorbs heavy metals in a pH dependent manner.

donax has been utilized in constructing wetlands for agricultural waste treatment (in combination with other species), and for the treatment of municipal wastewater. The ability to culture and regenerate A. donax will allow genetic transformation to be applied to the species. It then may be possible to generate transgenic variants for example with increased phytoremediation potential.

Among the advantages of the present method is the ability to obtain high frequency plant regeneration from immature inflorescences. Sustainable multiple shoot cultures have been established from giant reed where shoot elongation and rooting are controlled by the type and concentration of plant growth regulators in the synthetic culture medium. The in vitro grown plantlets are established easily in the soil.

Furthermore, it is believed that the efficiently produced plant clones can also be utilized for scientific research in physiology and genetics. Monocot tissues, at different stages of the in vitro propagation, are suitable for introduction of foreign genes. After such genetic modification, it should be possible to regenerate complete transgenic plants, and then to clonally propagate such transgenic individuals by this method. These efficient, large-scale micropropagation techniques would permit genetically modified clones of A. donax to be available in large numbers for industrial applications such as phytoremediation technologies in the field or in bioreactors.

The following examples describe preferred embodiments of the invention. Other embodiments within the scope of the claims herein will be apparent to one skilled in the art from consideration of the specification or practice of the invention as disclosed herein. It is intended that the specification, together with the examples, be considered to be exemplary only, with the scope and spirit of the invention being indicated by the claims which follow the examples. In the examples all percentages are given on a weight basis unless otherwise indicated.

EXAMPLE 1

This illustrates the formation of complete A. donax plantlets from excised tissue and shows the effect of different media upon shoot and root development.

Shoot tips bulging with developing inflorescences were collected from a large, naturalized patch of giant reed in the Southeastern United States in August. All but one of the leaf sheaths were stripped carefully so as not to expose the inflorescence. Shoot tips were disinfected by shaking in a solution of mercuric chloride plus 0.1% Tween 80 surfactant for 15 minutes. Shoot tips were rinsed three times with sterile water. The immature inflorescences were excised, chopped and placed on DM-8 or $II_1$-S medium in the dark or under continuous illumination (30-50 µmol $m^{-2}s^{-1}$, composed of a mixture of incandescent and fluorescent tubes— Sylvania and Power Twist Vita-Lite 40 W) at 26° C. to 28° C.

Callus was cultured every four weeks for maintenance. Regenerated and rooted plants were separated, potted in the greenhouse, and initially kept under plastic wrap cover to help acclimation.

DM-8 medium contained MS (Murashige and Skoog, 1975) basal salts (Sigma Fine Chemicals), 4.3 g/l; Miller's salt solution (6% w/v $KH_2PO_4$), 3 ml; myo-inositol, 100 mg/l; Vitamix (Marton and Browse, 1991), 2 ml; sucrose, 30 g/l; all mixed into water, supplemented with the plant growth regulators adenine hemisulfate, 80 mg/l; picloram, 0.12 mg/l; indole-3-butyric acid, 1 mg/l; 2,4-dichlorophenoxyacetic acid, 0.5 mg/l; isopentenelyadenine, 0.5 mg/l; trans-zeatin, 0.5 mg/l; and thidiazuron 3 mg/l; and solidified with Phytagel (Sigma Fine Chemicals) 2 g/l.

DM-3 medium differed only in the plant growth regulators, which were: adenine hemisulfate, 10 mg/l; 2,4-dichlorophenoxyacetic acid, 0.2 mg/l; thidiazuron, 0.1 μM.

DM-5 contained MS salts, 4.3 g/l; sucrose 30 g/l; thidiazuron, 0.1 μM.

Hormone-free medium was the same as DM-5, but without thidiazuron.

$II_1$-S medium contained MS basal salts, 4.3 g/l; $(NH_4)_2SO_4$, 200 mg/l; Miller's salt solution, 3 ml; myo-inositol, 200 mg/l; Vitamix, 2 ml; L-glutamine, 200 mg/l; sucrose, 30 g/l; mixed into sterile water, supplemented with the plant growth regulator, 2,4-dichlorophenoxyacetic acid, 1 mg/l; and solidified with agar (granulated, Fisher Scientific, Fair Lawn, N.J.), 2 g/l.

The pH of all tissue culture media was adjusted to 5.8 before sterilization in a pressure cooker at 109° C., 35 kPa pressure, for 25 minutes.

Sterile shoot tips containing immature inflorescences were cut into small cross-sectional segments (1-3 mm) and placed on two different media—$II_1$-S and DM-8. In three to four weeks, callus formed at the tips of pedicels and inflorescence stem segments and from flower parts. Callus on $II_1$-S medium was white and more or less translucent, without any sign of differentiation, and was not studied further. Callus on DM-8 medium was white and more or less translucent, initially without shoots, but soon displaying signs of differentiation and pale yellowish color. On DM-8 medium, etiolated shoots formed from the primary callus in the dark if left on the original medium for 4 to 6 weeks. Shoots often emerged from the florets. The mode of regeneration appeared to be multiple shoot formation from multiple meristems followed by microtillering.

The shoots turned green in two days after transfer to fresh shoot regeneration (DM-8) medium under light. Shoot differentiation progressed simultaneously with proliferation of green, regenerated callus. The subcultured callus showed various degrees of conversion to shoots.

Interestingly, the shoot regeneration medium could be used for shoot multiplication and production of complete plants as well. Small clusters of shoots, upon transfer to fresh medium, produced more shoots, and within one month further divisional was necessary. Many of the shoots elongated beyond 2 cm in length and developed roots (See Table 1), yielding 70-90 shoots per plate. The rate of shoot proliferation remained the same after subsequent cycles of subculture.

Shoot elongation varied, and it was necessary to separate shoots that elongated so much that it was impractical to subculture them in Petri dishes. The regenerating tissue was separated into two fractions: elongating shoots and initiating shoots.

TABLE 1

Effect of media on shoot regeneration and rooting of shoots (Means ± SE (n = 5)).

| MEDIUM | NO. OF ELONGATED SHOOTS PER GRAM TISSUE | PERCENT SHOOTS WITH ROOTS |
| --- | --- | --- |
| DM-8 | 19.6 ± 2.2 | 53 ± 2.4 |
| DM-5 | 21.8 ± 2.3 | 71 ± 5.7 |
| DM-3 light | 8.4 ± 1.2 | 56 ± 3.5 |
| DM-3 dark | 2.5 ± 0.3 | 55 ± 2.9 |

The elongating shoot clusters were transferred onto DM-5 medium in Magenta boxes with a low level of cytokinin (thidiazuron) where shoot proliferation continued. The DM-5 shoot proliferation medium have also been used for shoot multiplication and production of complete plants. As on DM-8, small clusters of shoots produced more shoots upon transfer to fresh medium. Most of the shoots elongated beyond 5 cm in length and developed roots (See Table 1) yielding 80 to 100 shoots per Magenta box. The rate of shoot proliferation remained the same after subsequent cycles of subculture. Complete plantlets or shoot clusters separated from the regenerating callus developed a healthy root system and the leaves elongated on hormone-free medium in Magenta boxes.

The fraction of tissue with initiating shoots from DM-8 medium was cultured on lowered cytokinin-level DM-3 medium either in the dark or under light. Callus on DM-3 medium is green under light and is completely covered with short shoots, and retained its original regeneration capacity for at least 18 months. The majority of the shoots did not elongate but kept multiplying (See Table 1). The same medium can be used for regenerating callus maintenance in the dark. Callus is pale yellow in the dark, and shoot multiplication is dominant over elongation (Table 1).

DM-3 medium in the dark thus makes it possible to have a long-term regenerating callus culture and to avoid loosing the regenerating callus via complete conversion to shoots. Shoot regeneration can be easily effected by transferring portions of callus onto DM-8, DM-5, or hormone-free medium. Over 200 individual plants were established and grown under growth chamber conditions without difficulty.

Somatic embryos were not detected in the present *A. donax* cultures under the conditions used. Without being bound by this or any other theory, it has been suggested that organization of single pole shoot meristems result from precocious germination of somatic embryos before complete development in graminoids which are characterized by regeneration occurring exclusively by somatic embryogenesis. See, e.g., Ozias-Akins, P. et al., *Protoplasma*, 110:417-420 (1982). However, the examples suggest that multiple shoot cultures can produce clones in high yield.

EXAMPLE 2

This example illustrates the preparation of complete plantlets from excised *A. donax* cell tissue.

Shoot tips bulging with developing inflorescences were collected from a large, naturalized patch of giant reed. All but one leaf sheath were stripped carefully so as not to expose the inflorescence. Shoot tips were disinfected by shaking in a solution of 5 times diluted commercial bleach solution containing 10% (v/v) ethanol and 0.1% Tween 80 surfactant (w/v) for 15 min. Shoot tips were rinsed three times with sterile water.

The immature inflorescences were excised, chopped, and placed on the primary solid culture medium containing (in mg l$^{-1}$, unless indicated otherwise) MS (Murashige and Skoog, 1975) basal salts (Sigma Fine Chemicals) 4,300 (which are nutrient salts); Miller's salt solution (6% [w/v] KH$_2$PO$_4$), 3 ml; myo-inositol, 100; Vitamix (Márton and Browse, 1991), 2 ml; sucrose, 30,000, supplemented with the plant growth regulators adenine, 80; 2,4-dichlorophenoxyacetic acid, 0.2; and thidiazuron, 0.1, and solidified with Gellan gum (Phytagel brand from Sigma Fine Chemicals), 2000. The primary explants were incubated in the dark at 25° C. for four weeks.

In three to four weeks, callus formed at the tips of pedicels and inflorescence stem segments and from flower parts. The callus was white and more or less translucent, initially without shoots, but soon displaying signs of differentiation and pale yellowish color. This regenerating tissue culture could be maintained for at least 3 years by subculturing every four weeks on the primary culture medium in the dark.

The shoots turned green in two days after transfer to secondary culture medium for shoot regeneration and multiplication under light. Continuous illumination was used (30-50 µmol m$^{-2}$s$^{-1}$; mixture of incandescent and cool white fluorescent tubes: Sylvania and Power-Twist Vita-Lite 40 W) at 25° C. Shoot differentiation progressed simultaneously with proliferation of green, regenerating callus. The subcultured callus showed various degrees of conversion to shoots.

The secondary medium contained (in mg l$^{-1}$, unless indicated otherwise) MS (Murashige and Skoog, 1975) basal salts (Sigma Fine Chemicals) 4,300; Miller's salt solution (6% [w/v] KH$_2$PO$_4$; sucrose, 30,000; supplemented with the plant hormone thidiazuron, 0.02, and solidified with Phytagel (Sigma Fine Chemicals), 2 g l$^{-1}$.

Small plantlets and clumps of multishoots were transferred to the tertiary culture medium, which differed from the secondary medium only in that it contained no hormones.

Figure 2:
FIG. 2 shows a photograph of *A. donax* plants six weeks after they were transferred to potting soil and which are clones that were grown by the present method from totipotent tissue culture tissue.
Figure 3:
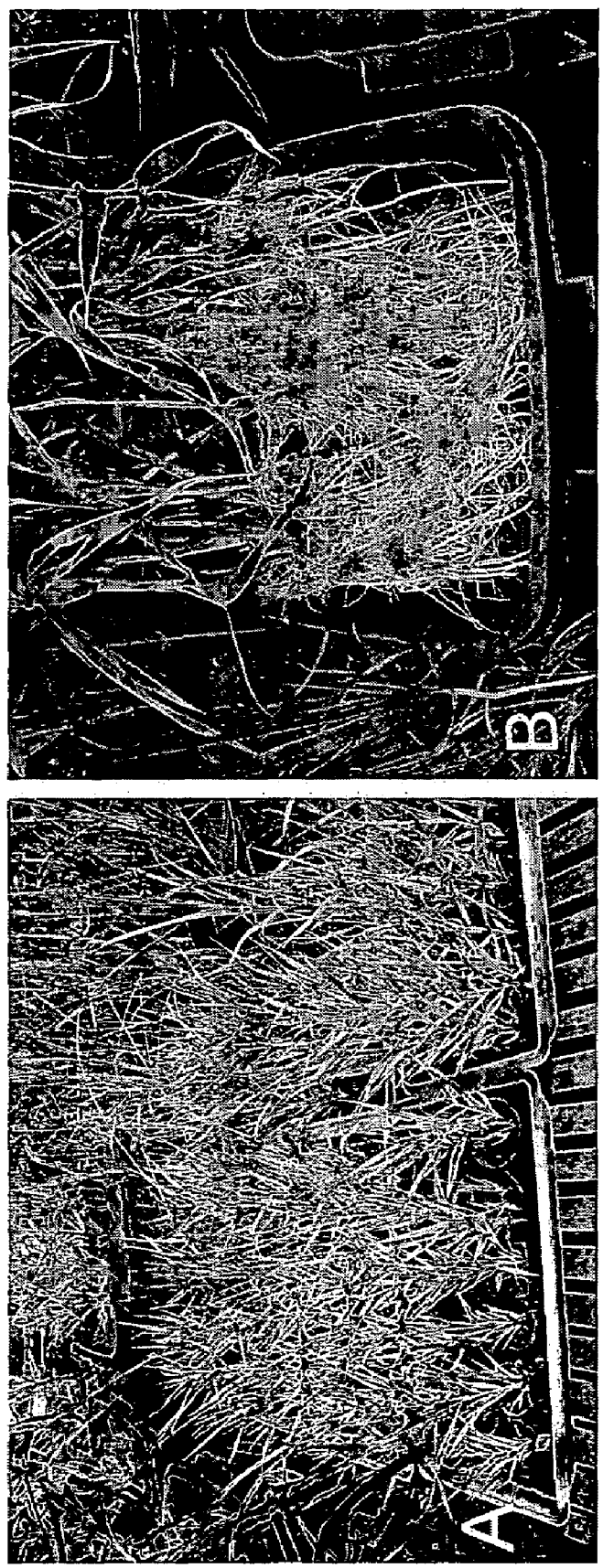
FIG. 3 shows (A) a photograph of plants six weeks after transfer potting soil, where the plants are clones of *A. donax* that were grown by the present method from totipotent tissue culture tissue, and (B), the extensive root system of *A. donax* plants grown in a standard liquid hydroponic medium.

Elongated and rooted plants were separated, then potted in the greenhouse, and initially kept under plastic wrap cover for 5 days to help acclimatization. FIG. 2 shows a photograph of (A) plants six weeks after they were transferred to potting soil. The plants shown are clones of *A. donax* that were grown by the present method from totipotent tissue culture tissue. FIG. 3 shows (A) the same six-week-old plants as shown in FIG. 2, along with (B) the extensive root system of *A. donax* plants grown in a standard liquid hydroponic medium.

The results of the observation for shoot formation after 4 weeks are shown in Table 2.

TABLE 2

Effect of media on shoot regeneration and rooting of shoots (means ± SE (n = 5)).

| Medium | No. of elongated shoots per g tissue | Percent shoots with roots |
|---|---|---|
| Primary | 8.4 ± 1.2 | 56 ± 3.5 |
| Secondary | 21.8 ± 2.3 | 71 ± 5.7 |

As evident from the table, both the number of the shoots formed from the tissue culture and the number shoots that developed roots increased upon transfer from the primary to the secondary medium.

EXAMPLE 3

This example illustrates the transfer and expression of a heterologous gene into *A. donax* tissue by the present method.

Cross-sectional segment of immature *A. donax* inflorescence were prepared and cultivated as described in Example 2. The totipotent tissue was cocultivated with *Agrobacterium tumefaciens* carrying plasmid pMSF3022, which carried the bar gene for positive selection in plant cells. The gene confers resistance to the antibiotic/herbicide phosphinothricin.

Cocultivation was carried out in 6 ml. of liquid primary culture medium for four days in the dark at room temperature. Explants were then rinsed with liquid medium and placed on solid selective and non-selective control medium containing the antibiotic/herbicide phosphinothricine at 10 mg/l. All medium contained tidarcillin at 400 mg/l to eliminate residual *A. tumefaciens*. Controls include explants incubated without *A. tumefaciens*. The efficacy of the gene transfer (and proof of expression) can be seen in FIG. 1, which shows the development of herbicide resistant embryogenic tissue on explants cocultivated with *Agrobacterium tumefaciens* (FIG. 1C). This can be contrasted with control explants (which were not contacted with *A. tumefaciens*) that were killed by 10 mg/l of phosphinothricin (FIG. 1A). Also shown are control explants that have developed callus in the absence of phosphinothricin (FIG. 1B), and cocultivated explants that have developed callus in the absence of phosphinothricin (FIG. 1D).

It was concluded, therefore, that the transfer of a heterologous gene into totipotent tissue occurred, and also that the gene was expressed in the cloned plants that were products of the titopotent tissue.

EXAMPLE 4

This example illustrates the operation of cloned plants of *A. donax* L. in a phytoreactor to cleanse organic waste materials from water.

Sustained titopotent cultures of *A donax* were grown as described in Example 2, and cloned plants derived from the titopotent tissues were established in a standard liquid hydroponic solution in plastic tubs (Shown in FIG. 4A). In one phytoreactor tub, trichloroethene (trichloroethylene) was added to a concentration of 0.25 mM. This was believed to be a high concentration of the organic material, because the allowable EPA concentration is 0.005 mg/l.

Figure 4:
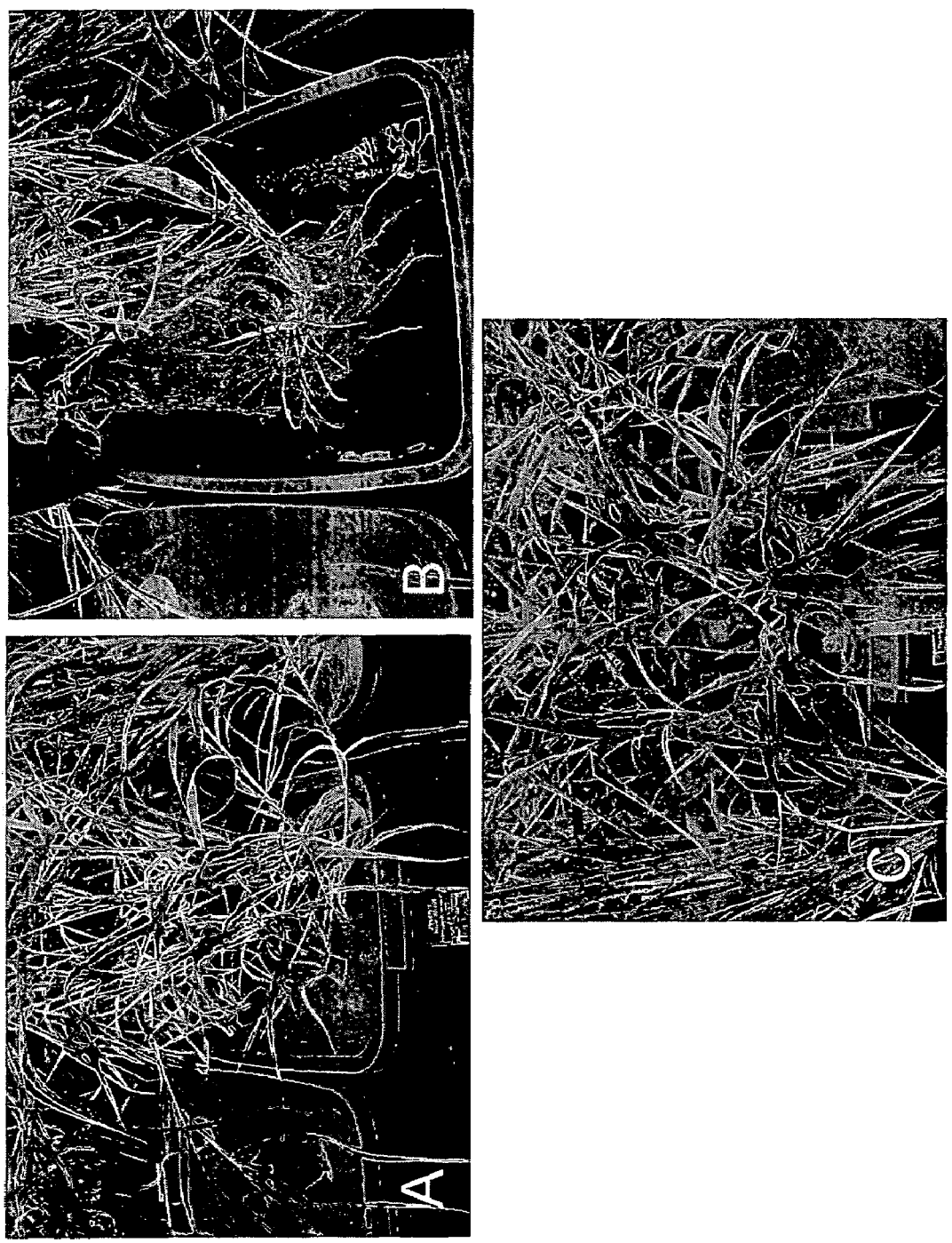
FIG. 4 illustrates the application of cloned *A. donax* plants in a phytoreactor system used to clean organic materials from water, where (A) shows the upper part of plants in a phytoreactor container suspended in a standard hydroponic medium, (B) shows the roots of *A. donax* plants after challenge with 0.25 mM trichloroethene solution, and (C) shows the roots of control plants; after 3 to 4 weeks, the roots of the challenged plants fully recovered and appeared to be the same as the control plants as shown in (C).

FIG. 4 illustrates the application of the cloned *A. donax* plants in the phytoreactor system, where (A) shows the upper part of plants in a phytoreactor container suspended in a standard hydroponic medium, (B) shows the roots of *A. donax* plants after challenge with 0.25 mM trichloroethene solution, and (C) shows the roots of control plants. After a recovery period of 3 to 4 weeks, the roots of the challenged plants fully recovered and appeared to be the same as the control plants as shown in (C).

It is believed that this shows evidence of the ability of the cloned *A. donax* plants to serve in phytoreactors for the remediation of wastewaters.

All references cited in this specification, including without limitation all papers, publications, patents, patent applications, presentations, texts, reports, manuscripts, brochures, books, internet postings, journal articles, periodicals, and the like, are hereby incorporated by reference into this specification in their entireties. The discussion of the references herein is intended merely to summarize the assertions made by their authors and no admission is made that any reference constitutes prior art. Applicants reserve the right to challenge the accuracy and pertinency of the cited references.

In view of the above, it will be seen that the several advantages of the invention are achieved and other advantageous results obtained.

As various changes could be made in the above methods and compositions without departing from the scope of the invention, it is intended that all matter contained in the above description and shown in the accompanying drawing shall be interpreted as illustrative and not in a limiting sense.

What is claimed is:

1. A method for the production of totipotent tissue culture of *Arundo donax*, the method comprising:
    selecting an explant of living tissue from the *Arundo donax*;
    cultivating the tissue on a primary medium which contains an auxin and a cytokinin to produce totipotent tissue; and
    transferring the totipotent tissue to a secondary medium containing a cytokinin and cultivating to produce plantlets having roots and shoots.

2. The method according to claim 1, comprising, in addition:
    moving the plantlets to a tertiary medium which is free of added plant hormones.

3. The method according to claim 1, wherein the explant comprises an inflorescence.

4. The method according to claim 1, wherein the explant is an immature inflorescence.

5. The method according to claim 1, wherein the auxin of the primary medium comprises 2,4-dichlorophenoxyacetic acid, picloram, and indolebutyric acid and the cytokinin of the primary medium comprises thidiazuron, zeatin, and dimethylallyladenine.

6. The method according to claim 1, wherein the cytokinin in the secondary medium is thidiazuron.

7. The method according to claim 1, further comprising acclimating the plantlets in soil.

8. The method according to claim 1, wherein the auxin of the primary medium is selected from the group consisting of 2,4-dichlorophenoxyacetic acid, picloram, and indolebutyric acid and the cytokinin of the primary medium is selected from the group consisting of benzyladenine, thidiazuron, zeatin, isopentyladenine, trans-zeatin, and dimethylallyladenine.

9. The method according to claim 1, wherein the auxin of the primary medium comprises 2,4-dichlorophenoxyacetic acid and picloram, and the cytokinin comprises benzyladenine, zeatin and thiadiazuron.

10. The method according to claim 1, wherein the auxin of the primary medium comprises 2,4-dichlorophenoxyacetic acid, indolebutyric acid, and picloram, and the cytokinin of the primary medium comprises adenine hemisulfate, isopentyladenine, trans-zeatin, and thiadiazuron.

11. The method according to claim 10, wherein the plant hormones are present in the following amounts in the primary medium: 2,4-dichlorophenoxyacetic acid, 0.5 mg/l; indolebutyric acid, 1.0 mg/l; picloram, 0.12 mg/l; adenine hemisulfate, 80 mg/l; isopentyladenine, 0.5 mg/l; trans-zeatin, 0.5 mg/l; and thiadiazuron, 3 mg/l.

12. The method according to claim 6, wherein the thiadiazuron is present at a concentration of 0.02 mg/l.

13. A method for the production of totipotent tissue culture of *Arundo donax*, the method comprising:
    selecting an explant of living tissue from the *Arunda donax*;
    cultivating the tissue on a primary medium which contains at least two different auxins and a cytokinin to produce totipotent tissue; and
    transferring the totipotent tissue to a secondary medium containing a cytokinin and cultivating to produce plantlets having roots and shoots.

14. The method according to claim 13, wherein the explant comprises an inflorescence.

15. The method according to claim 14, wherein the explant is an immature inflorescence.

16. The method according to claim 13, wherein the at least two auxins of the primary medium are selected from the group consisting of 2,4-dichlorophenoxyacetic acid, picloram, and indolebutyric acid and the cytokinin of the primary medium is selected from the group consisting of benzyladenine, thidiazuron, zeatin, isopentyladenine, trans-zeatin, and dimethylallyladenine.

17. The method according to claim 13, wherein the auxin of the primary medium comprises 2,4-dichlorophenoxyacetic acid, picloram, and indolebutyric acid and the cytokinin of the primary medium comprises thidiazuron, zeatin, and dimethylallyladenine.

18. The method according to claim 13, wherein the auxin of the primary medium comprises 2,4-dichlorophenoxyacetic acid and picloram, and the cytokinin comprises benzyladenine, zeatin and thiadiazuron.

19. The method according to claim 13, wherein the auxin of the primary medium comprises 2,4-dichlorophenoxyacetic acid, indolebutyric acid, and picloram, and the cytokinin of the primary medium comprises adenine hemisulfate, isopentyladenine, trans-zeatin, and thiadiazuron.

20. The method according to claim 13, wherein the plant hormones are present in the following amounts in the primary medium: 2,4-dichlorophenoxyacetic acid, 0.5 mg/l; indolebutyric acid, 1.0 mg/l; picloram, 0.12 mg/l; adenine hemisulfate, 80 mg/l; isopentyladenine, 0.5 mg/l; trans-zeatin, 0.5 mg/l; and thiadiazuron, 3 mg/l.

21. The method according to claim 13, wherein the cytokinin in the secondary medium is thidiazuron.

22. The method according to claim 21, wherein the thiadiazuron is present at a concentration of 0.02 mg/l.

23. The method according to claim 13, further comprising acclimating the plantlets in soil.

24. The method according to claim 22, further comprising acclimating the plantlets in soil.

* * * * *

UNITED STATES PATENT AND TRADEMARK OFFICE
CERTIFICATE OF CORRECTION

| | | |
|---|---|---|
| PATENT NO. | : 7,303,916 B2 | |
| APPLICATION NO. | : 10/982254 | |
| DATED | : December 4, 2007 | |
| INVENTOR(S) | : Laszlo Marton and Mihaly Czako | |

It is certified that error appears in the above-identified patent and that said Letters Patent is hereby corrected as shown below:

On Title Page item 56
Page 2, Right Column:
Line 1 of the 11th reference, replace the term "*donax*for" with the term -- *donax* for --.

Column 7:
Line 63, replace the term "mol" with the term -- µmol --.

Signed and Sealed this

Twenty-ninth Day of April, 2008

JON W. DUDAS
*Director of the United States Patent and Trademark Office*